(12) United States Patent
Lentell

(10) Patent No.: US 6,890,352 B1
(45) Date of Patent: May 10, 2005

(54) VESSEL VALVE

(75) Inventor: Jan Lentell, Värmdö (SE)

(73) Assignee: JCL Technic AB, Almunge (SE)

( * ) Notice: Subject to any disclaimer, the term of this patent is extended or adjusted under 35 U.S.C. 154(b) by 274 days.

(21) Appl. No.: 10/149,017

(22) PCT Filed: Nov. 9, 2000

(86) PCT No.: PCT/SE00/02197

§ 371 (c)(1),
(2), (4) Date: Jul. 12, 2002

(87) PCT Pub. No.: WO01/43666

PCT Pub. Date: Jun. 21, 2001

(30) Foreign Application Priority Data

Dec. 14, 1999 (SE) .............................. 9904569

(51) Int. Cl.[7] .................................. A61F 2/06
(52) U.S. Cl. .................... 623/2.27; 623/2.31; 623/2.33; 623/2.28
(58) Field of Search .............................. 623/1, 2, 1.24, 623/2.2, 2.27, 2.28, 2.3–2.33, 900, 23, 68; 606/191–198

(56) References Cited

U.S. PATENT DOCUMENTS

| | | |
|---|---|---|
| 3,938,197 A | 2/1976 | Milo |
| 4,820,299 A | 4/1989 | Philippe et al. |
| 5,078,739 A | 1/1992 | Martin |
| 5,628,792 A | 5/1997 | Lentell |
| 5,776,188 A * | 7/1998 | Shepherd et al. .......... 623/2.38 |
| 5,861,028 A | 1/1999 | Angell |
| 6,068,657 A * | 5/2000 | Lapeyre et al. .............. 623/2.2 |
| 6,395,024 B1 * | 5/2002 | Lapeyre et al. ............ 623/2.22 |

FOREIGN PATENT DOCUMENTS

| | | |
|---|---|---|
| WO | 88/02247 | 4/1988 |
| WO | WO 93/17637 | 9/1993 |

* cited by examiner

*Primary Examiner*—David J. Isabella
*Assistant Examiner*—Urmi Chattopadhyay
(74) *Attorney, Agent, or Firm*—Burns, Doane, Swecker & Mathis, L.L.P.

(57) ABSTRACT

A vessel valve including a sleeve or ring having a central opening and openable and closeable flap elements intended to allow the flow of blood through the central opening in one direction, whereas the flap elements are designed as circle segments, and the sector angle is $$\frac{360°}{n}$$

wherein n is a number of circle segments and is equal to 3, 4, 5 or 6, and wherein each flap element at its outer edge is pivotably connected to an inwardly directed flange on the inside of the ring so that in a closed position they co-operate to form a sealing body and in an open position they allow free passage of blood. The ring is composed of n sections, whose pair-wise juxtaposed ends form recesses in the flange accommodating hinge elements which are arranged in the middle of the outer edge of each of the flap elements and which with assembled sections are locked by undercutting; and a method for the manufacture of such vessel valve.

17 Claims, 1 Drawing Sheet

US 6,890,352 B1

VESSEL VALVE

TECHNICAL FIELD

The present invention relates to implantable back valves to be placed in vessels of living creatures including man. The invention is particularly related to so called cardiac valves, in other words heart valves, intended to allow flow of blood in one direction in a blood path in connection to the heart of a living mammal, comprising man. Even if the invention is not restricted hereto it will be described in the following mainly in connection with cardiac valves, so called heart valves.

BACKGROUND OF THE INVENTION

Cardiac valves, so called heart valves, are found in a number of embodiments made both of wholly artificial materials, such as titanium, pyrolytic carbon or the like, or manufactured from natural tissue of porcine or bovine origin, said materials being treated in a chemical manner so as to obtain desirable properties. All hitherto known back valves for such intended function are associated with severe disadvantages, among which the following may be mentioned.

The designs not based on natural tissue are all made as more or less complicated constructions which result in risk of failure or unsatisfactory function in other ways. Known valves are, furthermore, designed so as to occupy, in an open position, an essential part of the flow cross-section, thus offering resistance to the flow of blood. Many of the known valves are furthermore designed in an asymmetric way with concomitant inconveniences. Finally, it can be mentioned that known valves often are associated with inertia in their opening or closing movement which substantially reduces their efficiency.

U.S. Pat. No. 5,078,739 relates to a cardiac valve said to be capable of replacing any one of the four valves of the heart. This known valve includes a ring having a central opening and two valve flaps arranged to open and close. This construction results in the disadvantage that an asymmetric flow pattern is created with concomitant turbulence and undesired deposits.

U.S. Pat. No. 4,820,299 describes a cardiac valve having three valve elements for opening and closing each provided with a hinge arrangement to the surrounding ring. One part of the hinge arrangement is constituted by a yoke directed inwardly into the flow of blood, whereby disturbances arise in the flow of blood and thereby non-desired deposits of coagulated blood. Furthermore, the construction means that in the open state spaces are formed between the exterior surface of the valve elements and the interior surface of the ring through which blood can flow at the side of the main flow, and also this condition results in non-desired flow profiles creating conditions for deposits in an undesired way.

In PCT-application SE93/00219 there is described a coronary valve, so called heart valve, comprising a sleeve or a ring having a central opening and three flap elements for opening and closing giving the valve the function of a back valve. The flap elements are pivotably connected to the inside of the ring at one end thereof, and each hinge contains a pin or stud which is attached to the ring in a tangentially extending aperture therein. The disadvantage of this known construction is that these pins or studs are arranged in a through-hole in the ring whereby blood can enter into these holes both from the inside and from the outside. Since such blood present around the pin is stationary and not continually replaced problems arise in the form of deposits of coagulated blood and thereby associated problems.

SUMMARY OF THE INVENTION

The present invention has for an object to provide a cardiac valve by which the prior art disadvantages are eliminated or at any rate essentially reduced.

Another object of the invention is to provide a cardiac valve which is designed in such a way that it does not result in stationary collection of blood, particularly in relation to hinge mechanisms.

Yet another object of the invention is to provide a valve where the flap elements in open position define a unitary flow passage for the blood, whereby flow outside of the backside of the valve elements is substantially avoided.

For these and other objects which will be clear from the following description the cardiac valve according to the invention comprises a sleeve or ring having a central opening 5 and openable and closeable flap elements 7 intended to allow the flow of the blood through the central opening 5 in one direction, whereas the flap elements 7 are designed as circle segments, wherein the sector angle is $$\frac{360°}{n}$$

wherein n is a number of circle segments and is equal to 3, 4, 5 or 6, and wherein said flap element 7 at its outer edge is pivotably connected to an inwardly directed flange 9 on the inside of ring 3 so that in closed position they co-operate to form a sealing body and in open position allow free passage of blood. The valve is characterized in that the ring is composed of n sections, whose pair-wise juxtaposed ends form recesses 11 in the flange 9 accommodating hinge elements 13 which are arranged in the middle of the outer edge of each of the flap element 7 and which with assembled sections are locked by undercutting.

It is preferred that the number of flap elements is three, whereby a symmetric flow passage is obtained at the same time as the number of movable parts of the valve is limited.

In the closed position of the valve the flap elements suitably form a cone of obtuse peak angle, preferably lying within the range about 150 to about 175°.

The cardiac valve according to the present invention is preferably designed in such a way that the inwardly directed flange has a side surface against which the outer edges of the flap elements rest in sealing co-operation, and it is particularly preferred that the attachment of the flap elements to the ring is shaped in such a manner that one flap element alone cannot be folded to a position substantially exceeding the position it has in co-operation with the other flap elements.

The recesses found in connection with the oppositely placed ends of the sections preferably comprise opposite semi-spheres arranged at a distance from each other. In these separate semi-spheres semi-spherical extensions are arranged on the hinge element and pivotably anchored by undercut locking. It is particularly preferred that the flap element is flat and made in one piece with the flap element.

For the purpose of reducing the flow of blood on the outside of the flap elements when in open position it is preferred that the distance between the semi-spheres corresponds to a sector angle of about 10 to about 20°.

To enable attachment by stitching of the cardiac valve according to the invention it is suitably provided with a stitch ring surrounding the assembled sections forming the ring. This surrounding stitch ring is provided with a circumferential outwardly directed flange containing axial holes evenly distributed around the flange, whereby suture stitching can be made.

In view of the fact that the sleeve or ring is built up from a number of sections corresponding to the number of valve elements it is suitable that the sections are made from a material whereby the sections can be bound together and which at the same time is biocompatible. The attachment between the sections is preferably made by welding or fusion with the sections made by a weldable or fusible metal. This metal is preferably stainless steel or titanium.

The invention also relates to a method for the manufacture of a valve as described above. The manufacture takes place by assembling the sections after positioning of the flap elements with the hinge elements accommodated in the respective recesses with simultaneous undercut locking of the flap elements via the hinge elements.

BRIEF DESCRIPTION OF THE DRAWINGS

The present invention-will in the following be described further with reference to a preferred embodiment illustrated in the appended drawing. In the drawing.

DETAILED DESCRIPTION OF A PREFERRED EMBODIMENT

Figure 4:
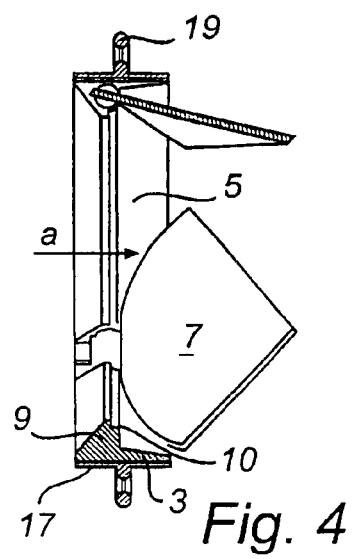
FIG. 4 shows a side view partly in section along line A—A in FIG. 3.
Figure 6:
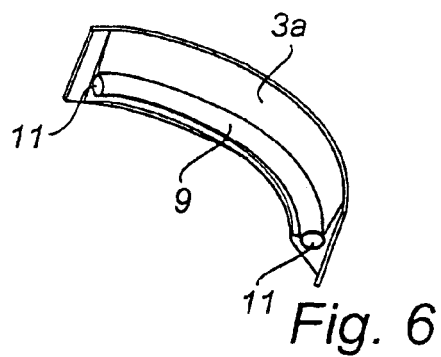
FIG. 6 shows a perspective view of a section part of the ring of the valve.

The embodiment shown in the drawing is particularly useful for use as a cardiac valve or so called heart valve and is shown in a scale of about 2:1. The cardiac valve consists in principle of a sleeve or ring 3 having a central passage 5, through which blood can pass the valve in the direction of arrow a with the valve in open position (FIG. 4). The ring 3 is composed of three sections 3a, 3b, 3c, one being shown in perspective in FIG. 6, and these three sections are attached to each other in a suitable manner, for example by welding with the valve made of a biocompatible metal, for example stainless steel or titanium.

The sleeve or ring 3 is provided with a radially inwardly directed circular flange 9, three flap elements 7 being pivotably connected in a manner to be described further below.

Figure 2:
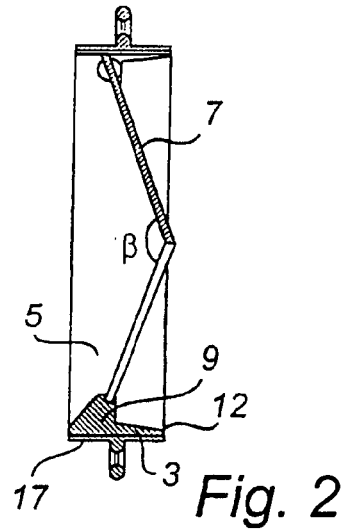
FIG. 2 shows a side view partly in section along line A—A of FIG. 1.

Thus, ring 3 contains three flap elements 7, of which each is designed as a circle segment as seen in the plan of the paper, where the sector angle α thus is 120°. In a closed position flap elements 7 form a conical body having a peak angle β (FIG. 2) which in the embodiment shown is about 170°. This peak angle can, of course, be greater but does suitably not exceed 180°.

Each flap element 7 is at the outer edge provided with a hinge element 13 which is provided with two opposite semi-circular extensions 15 intended to be accommodated in recesses in the oppositely placed ends of sections 3a, 3b, 3c by recesses at said ends comprising semi-spherical cavities 11.

The inwardly directed flange 9 of ring 3 is provided with a side surface 10, against which the outer edges of the flap elements rest in sealing co-operation. The end position of flap elements 7 in an open state is limited by the inside of the upper edge 12 of ring 3. In this manner unnecessary stresses on the hinges are avoided. Flange 9 with side surface 10 has further for a function to prevent that one individual flap element 7 can move in the closing direction past the position according to FIG. 2 determined by the sealing co-operation between the flap elements 7.

To enable anchorage of the cardiac valve in position in the body by stitching the valve is provided with a stitch ring 17 surrounding ring 3. This stitch ring 17 is provided with a circumferential outwardly directed flange 19 containing axial holes 21 evenly distributed around the flange. When using metal in the valve construction shown stitch ring 17 is suitably passed on to ring 3 by shrinkage and attachment to ring 3 by circumferential welding at both ends of the ring.

Figure 1:
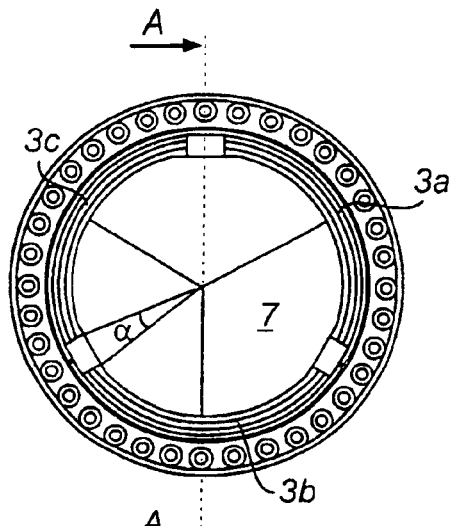
FIG. 1 shows a plan view of a vessel valve in accordance with the invention.
Figure 3:
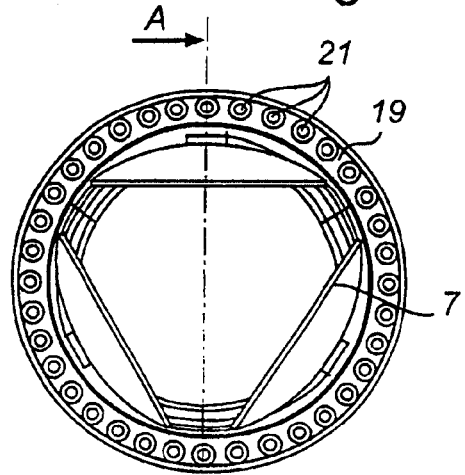
FIG. 3 shows the vessel valve according to FIG. 1 in open position.

In FIG. 3 there is shown a plan view of the cardiac valve in an open position. As is clear from this plan view the blood is essentially prevented from flowing on the outside of flap elements 7 in this open position. This is obtained by the fact that the distance between the semi-spherical recesses 11 in the assembled ring is limited so that said distance corresponds at most to a sector angle α of about 200 (FIG. 1). At the opposite extreme the sector angle α is restricted for practical reasons in that the hinge element 13 cannot be designed below a certain dimension.

Figure 5:
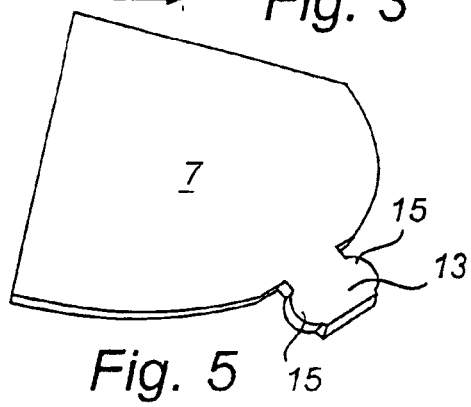
FIG. 5 shows a perspective view of the flap element.

FIG. 5 shows a perspective view of one individual hinge element 7. Hinge element 7 can in a simple manner be made from one piece by cutting from a metal sheet, for example of titanium, whereby also hinge element 13 obtains a flat shape. Practical experiments have shown that this is a particularly preferred design, since in connection with opening and closing of the valve by the movement of the flap elements the hinge elements 13 having the semi-spherical extensions 15 "sweep" the space within the semi-spherical recesses 11 thereby avoiding collection of stationary blood. In this manner every assembly of blood in all corners of the valve are avoided with the cardiac valve according to the present invention thereby avoiding undesired deposits.

In the final assemble form of the cardiac valve with sections 3a, 3b, 3c welded together and the stitch ring 17 assembled onto ring 3 and welded thereto there is obtained a construction acting as a unitary body obtaining only four parts, namely in addition to rings 3, 17 the pivotably mounted flap elements 7.

For use of the vessel valve as a cardiac valve the number of evenly distributed axial holes 21 at a valve diameter of about 27 mm may preferably exceed about 20 and be present in a number of for example about 40. In view of the fact that the circumferential outwardly directed flange 19 on the stitch ring 17 is placed symmetrically in the middle of the stitch ring there is also obtained the advantage that the valve with its function as a back valve can be placed in either of two directions. It can be added that the cardiac valve according to the present invention can be used both in aorta and mitrally or in blood passages requiring back valve function.

The present invention is not restricted to the embodiment described above with regard to constructional details or otherwise. It can, of course, be modified within the scope of the definition given in the appended claims.

What is claimed is:

1. Vessel valve comprising a sleeve or ring having a central opening and openable and closeable flap elements intended to allow the flow of blood through the central opening in one direction, the flap elements are designed as circle segments, wherein the sector angel is $$\frac{360°}{n}$$

and wherein n is a number of circle segments and is equal to 3, 4, 5 or 6, and wherein each flap element at its outer edge is pivotably connected to an inwardly directed flange on the inside of the sleeve or ring so that in closed position they co-operate to form a sealing body and in open position allow free passage of blood, wherein the sleeve or ring is composed of n sections, whose pair-wise juxtaposed ends form recesses in the flange accommodating hinge elements which are arranged in the middle of the outer edge of each of the flap elements and which with assembled sections are locked by undercutting, wherein said recesses comprise juxtaposed semi-spheres arranged at a distance from each other and between which the hinge element provided with a corresponding semi-spheric extension is pivotably anchored, and wherein the hinge element is flat and designed in one piece with the flap element.

2. Vessel valve according to claim 1, wherein the number of flap elements is three.

3. Vessel valve according to claim 2, wherein the flap elements together form a cone of obtuse peak angle β.

4. Vessel valve according to claim 2, wherein said inwardly directed flange has a side surface against which the outer edges of the flap elements rest in sealing co-operation.

5. Vessel valve according to claim 2, by further comprising a stitch ring surrounding said sections, said stitch ring being provided with a circumferential outwardly directed flange provided with axial holes evenly distributed around the flange.

6. Vessel valve according to claim 2, wherein said vessel valve is made from a biocompatible material parts of which can be joined together.

7. Vessel valve according to claim 1, wherein the flap elements together form a cone of obtuse peak angle β.

8. Vessel valve according to claim 7, wherein said peak angle β lies within the range about 150–175°.

9. Vessel valve according to claim 7, said inwardly directed flange has a side surface against which the outer edges of the flap elements rest in sealing co-operation.

10. Vessel valve according to claim 1, wherein said inwardly directed flange has a side surface against which the outer edges of the flap elements rest in sealing co-operation.

11. Vessel valve according to claim 10, wherein the attachment of the flap elements to the sleeve or ring is shaped in such a manner that one flap element alone cannot be folded to a position substantially exceeding the position it has in co-operation with the other flap elements.

12. Vessel valve according to claim 1, wherein said distance between the semi-spheres corresponds to a sector angle of about 10 to about 20°.

13. Vessel valve according to claim 1, further comprising a stitch ring surrounding said sections, said stitch ring being provided with a circumferential outwardly directed flange provided with axial holes evenly distributed around the flange.

14. Vessel valve according to claim 1, wherein said vessel valve it is made from a biocompatible material parts of which can be joined together.

15. Vessel valve according to claim 14, wherein said material is a metal capable of joining by welding or fusion.

16. Vessel valve according to claim 15, wherein said material is selected from the group consisting of stainless steel end titanium.

17. A method for the manufacture of a vessel valve comprising a sleeve or ring having a central opening and openable and closeable flap elements intended to allow the flow of the blood through the central opening in one direction, the flap elements are designed as circle segments, wherein the sector angle is $$\frac{360°}{n}$$

wherein n is a number of circle segments and is equal to 3, 4, 5 or 6, and wherein each flap element at its outer edge is pivotably connected to an inwardly directed flange on the inside of the sleeve or ring so that in closed position they co-operate to form a sealing body and in open position allow free passage of blood, wherein each of the flap elements is provided with a hinge element arranged in the middle of the outer edge of the flap element, wherein the sleeve or ring is composed of n sections, the pair-wise juxtaposed ends of the n sections forming recesses in the flange, and wherein, after positioning of the flap elements with the hinge elements accommodated in the respective recesses, the n sections are joined together with undercut interlocking of the flap elements via said hinge elements, wherein said recesses comprise juxtaposed semi-spheres arranged at a distance from each other and between which the hinge element provided with a corresponding semi-spheric extension is pivotably anchored, and wherein the hinge element is flat and designed in one piece with the flap element.

* * * * *

UNITED STATES PATENT AND TRADEMARK OFFICE
CERTIFICATE OF CORRECTION

PATENT NO. : 6,890,352 B1
DATED : May 10, 2005
INVENTOR(S) : Jan Lentell

It is certified that error appears in the above-identified patent and that said Letters Patent is hereby corrected as shown below:

Column 5,
Line 1, delete "angel" and insert -- angle --.

Signed and Sealed this

Twenty-seventh Day of September, 2005

JON W. DUDAS
*Director of the United States Patent and Trademark Office*